(12) United States Patent
DeNatale et al.

(10) Patent No.: US 10,416,246 B2
(45) Date of Patent: Sep. 17, 2019

(54) PHYSICS PACKAGE FOR COMPACT ATOMIC DEVICE

(71) Applicant: TELEDYNE SCIENTIFIC & IMAGING, LLC., Thousand Oaks, CA (US)

(72) Inventors: Jeffrey F. DeNatale, Thousand Oaks, CA (US); Robert L. Borwick, III, Thousand Oaks, CA (US); Philip A. Stupar, Oxnard, CA (US); Viktor Tarashansky, Agoura Hills, CA (US)

(73) Assignee: TELEDYNE SCIENTIFIC & IMAGING, LLC, Thousand Oaks, CA (US)

( * ) Notice: Subject to any disclaimer, the term of this patent is extended or adjusted under 35 U.S.C. 154(b) by 131 days.

(21) Appl. No.: 15/582,397

(22) Filed: Apr. 28, 2017

(65) Prior Publication Data

US 2018/0313913 A1 Nov. 1, 2018

(51) Int. Cl.
| | |
|---|---|
| G01C 19/60 | (2006.01) |
| G01R 33/26 | (2006.01) |
| G04F 5/14 | (2006.01) |
| H03B 17/00 | (2006.01) |
| H03L 7/26 | (2006.01) |
| G01R 33/28 | (2006.01) |
| G01R 33/24 | (2006.01) |
| H01F 27/24 | (2006.01) |
| H01F 17/00 | (2006.01) |
| A61N 2/02 | (2006.01) |
| A61N 5/06 | (2006.01) |
| H01F 5/00 | (2006.01) |
| H01F 7/20 | (2006.01) |

(52) U.S. Cl.
CPC .............. *G01R 33/288* (2013.01); *A61N 2/02* (2013.01); *A61N 5/0624* (2013.01); *G01R 33/24* (2013.01); *G01R 33/26* (2013.01); *G04F 5/145* (2013.01); *H01F 17/0013* (2013.01); *H01F 27/24* (2013.01); *H03B 17/00* (2013.01); *H03L 7/26* (2013.01); *G01C 19/60* (2013.01); *H01F 5/003* (2013.01); *H01F 7/20* (2013.01)

(58) Field of Classification Search
CPC ........ G01C 19/60; G01R 33/24; G01R 33/26; G04F 5/14; G04F 5/145; H03B 17/00; H03L 7/26
USPC ............................................. 331/3, 68, 94.1
See application file for complete search history.

(56) References Cited

U.S. PATENT DOCUMENTS

| | | | | |
|---|---|---|---|---|
| 3,382,452 A * | 5/1968 | Rempel | ...................... | H03L 7/26 331/3 |
| 3,798,565 A * | 3/1974 | Jechart | ...................... | H03L 7/26 331/3 |
| 4,494,085 A * | 1/1985 | Goldberg | ............. | G01N 24/006 324/304 |
| 6,265,945 B1 * | 7/2001 | Delaney | .................. | G04F 5/145 331/3 |
| 6,320,472 B1 * | 11/2001 | Vanier | ..................... | G04F 5/145 331/94.1 |

(Continued)

*Primary Examiner* — Levi Gannon
(74) *Attorney, Agent, or Firm* — K&L Gates LLP (57) ABSTRACT

A physics package apparatus for a compact atomic device includes a container having a plurality of slots and an open end, a first vapor cell carrier slidably seated in one of the plurality of slots, a vapor cell coupled to the first vapor cell carrier; and a lid sealably enclosing the open end so that the vapor cell is sealably enclosed in the container.

21 Claims, 10 Drawing Sheets

(56) References Cited

U.S. PATENT DOCUMENTS

| | | | |
|---|---|---|---|
| 2013/0265042 A1* | 10/2013 | Kawabata | G01R 33/26 324/301 |
| 2014/0232478 A1* | 8/2014 | Maki | H03B 17/00 331/94.1 |
| 2014/0293551 A1* | 10/2014 | Chindo | H01S 5/0687 361/728 |
| 2015/0180490 A1* | 6/2015 | Chindo | H03L 7/26 331/94.1 |
| 2017/0141783 A1* | 5/2017 | Tanaka | H03L 1/02 |
| 2017/0279455 A1* | 9/2017 | Maki | H03L 1/02 |

* cited by examiner

PHYSICS PACKAGE FOR COMPACT ATOMIC DEVICE

STATEMENT REGARDING FEDERALLY SPONSORED RESEARCH OR DEVELOPMENT

This invention was made with Government support under Contract No. W15P7T-10-C-A019 awarded by the US Army Communications-Electronics Research, Development and Engineering Center. The Government has certain rights in the invention.

BACKGROUND

Field of the Invention

The field of the invention relates to physics packages for atomic devices such as atomic clocks, magnetometers or gyroscopes.

Description of the Related Art

Chip-scale atomic devices such as chip-scale atomic clocks ("CSAC") may involve the interrogation of atomic states in a vapor cell that typically contains alkali species and buffer gasses. The physics packages of these devices are typically constructed using an assembly of multiple component subsystems: an optical source, usually a vertical-cavity surface-emitting laser ("VCSEL"); conditioning optics; a vapor cell; and photodetector. These components must be held in given positions to maintain reproducibility of the optical interrogation. The VCSEL and vapor cell must be thermally biased to stabilize temperature and allow control over a range of external ambient conditions, and the assembly must allow electrical interconnect to the VCSEL, vapor cell, and photodetector modules. Controlled magnetic fields typically must be applied to generate the necessary atomic states in the alkali vapor. These constraints can make assembly difficult, often precluding use of automated assembly technologies and increasing assembly and packaging costs. A need exists to simplify assembly methods and to reduce packaging costs.

SUMMARY

A physics package apparatus for a compact atomic device includes a container having a plurality of slots and an open end, a first vapor cell carrier slidably seated in one of the plurality of slots, a vapor cell coupled to the first vapor cell carrier, and a lid sealably enclosing the open end, so that the vapor cell is sealably enclosed in the container.

Another embodiment of an apparatus includes a container having a plurality of carrier slots, a photodetector coupled to a photodetector carrier, the photodetector carrier removably seated in a first carrier slot of the plurality of carrier slots, a VCSEL coupled to a VCSEL carrier, the VCSEL carrier removably seated in a second one of the plurality of carrier slots, a vapor cell slidably seated in the container, and a lid sealably enclosing a top side of the container so that the vapor chamber, photodetector and VCSEL are sealably enclosed in the container.

BRIEF DESCRIPTION OF THE DRAWINGS

The components in the figures are not necessarily to scale, emphasis instead being placed upon illustrating the principals of the invention. Like reference numerals designate corresponding parts throughout the different views.

DETAILED DESCRIPTION

A physics package apparatus for a compact atomic device is disclosed that provides for simplified assembly methods and reduced packaging costs. The package may include a container having a plurality of slots and an open end. The slots may be configured to slidably accept and thereby align a variety of component parts of chip-scale atomic devices seated on respective carriers. For example, a vapor cell may be coupled to a vapor cell carrier to be slidably received into one of the container's slots. Similarly, a vertical-cavity surface-emitting laser ("VCSEL") and VCSEL carrier may be slidably received into another one of the slots to establish spacing and alignment with the vapor cell. Either the lid or the slots themselves may have electrical contacts that are in electrical communication with electrical pads on an exterior of the container. A lid may enclose the open end to sealably enclose each component in the container.

Figure 1:
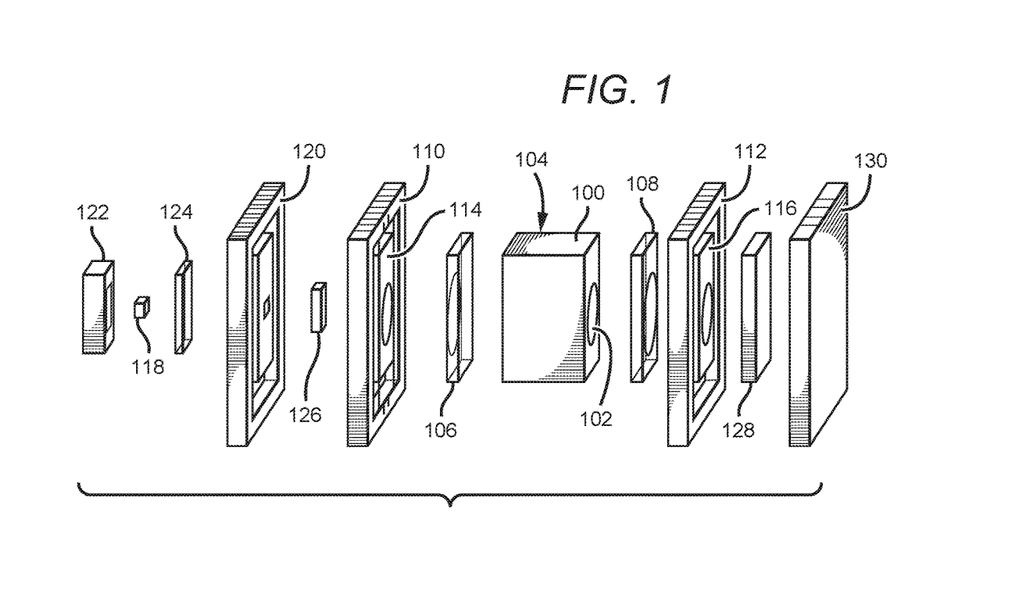
FIG. 1 is an exploded perspective view of one embodiment of an atomic clock physics package having a vapor cell, photodetector, and VCSEL laser source that may be removably inserted into a sealable slotted container.

FIG. 1 is an exploded perspective view of one embodiment of an atomic clock physics package having a vapor cell, photodetector, and VCSEL laser source that may be removably inserted into a sealable slotted container, subsequent to individual assembly and independent testing, and a lid having interior electrical contacts to exchange signals with the interior vapor cell, photodetector, and VCSEL laser source. A vapor cell substrate 100 having an interrogation chamber 102 (collectively a "vapor cell" 104) may be sealed on opposite sides of the interrogation chamber with first and second glass windows (106, 108). The vapor cell 104 and glass windows (106, 108) may be suspended between first and second vapor cell carriers (110, 112) that are each a three-dimensional rigid frame. Each vapor cell carrier (110, 112) may have a respective suspension structure (114, 116) made from a low thermal conductivity material, such as Kapton™ polyimide film or Cirlex™ polymide laminate offered by DuPont USA of Torrence, Calif. ("a suspension structure"). The suspension structure (114, 116) may be attached to the frame and extend into a center region of the frame for suspending and thermally isolating the vapor cell from the remainder of the two vapor cell carriers (110, 112). The VCSEL 118 may be coupled to a VCSEL substrate carrier 120 through a VCSEL substrate 122. The VCSEL substrate carrier 120 may be formed as a three-dimensional rigid frame. A neutral density (ND) filter 124 may also be coupled to the VCSEL carrier 120 and positioned to receive light emitted from the VCSEL 118. A wave plate polarizer 126, preferably consisting of a linear polarizer and a quarter wave plate, may also be coupled to the VCSEL carrier 120 and positioned to receive light (not shown) emitted from the VCSEL 118. The VCSEL 118, neutral density filter 124, wave plate polarizer 126 are aligned so that light emitted from the VCSEL 118 passes through each (124, 126) to interrogate the vapor cell 104. A photodetector 128 seated on a photodetector carrier 130 is positioned to receive the VCSEL light when emitted from the VCSEL 118 and transmitted through the vapor cell 100.

Figure 2:
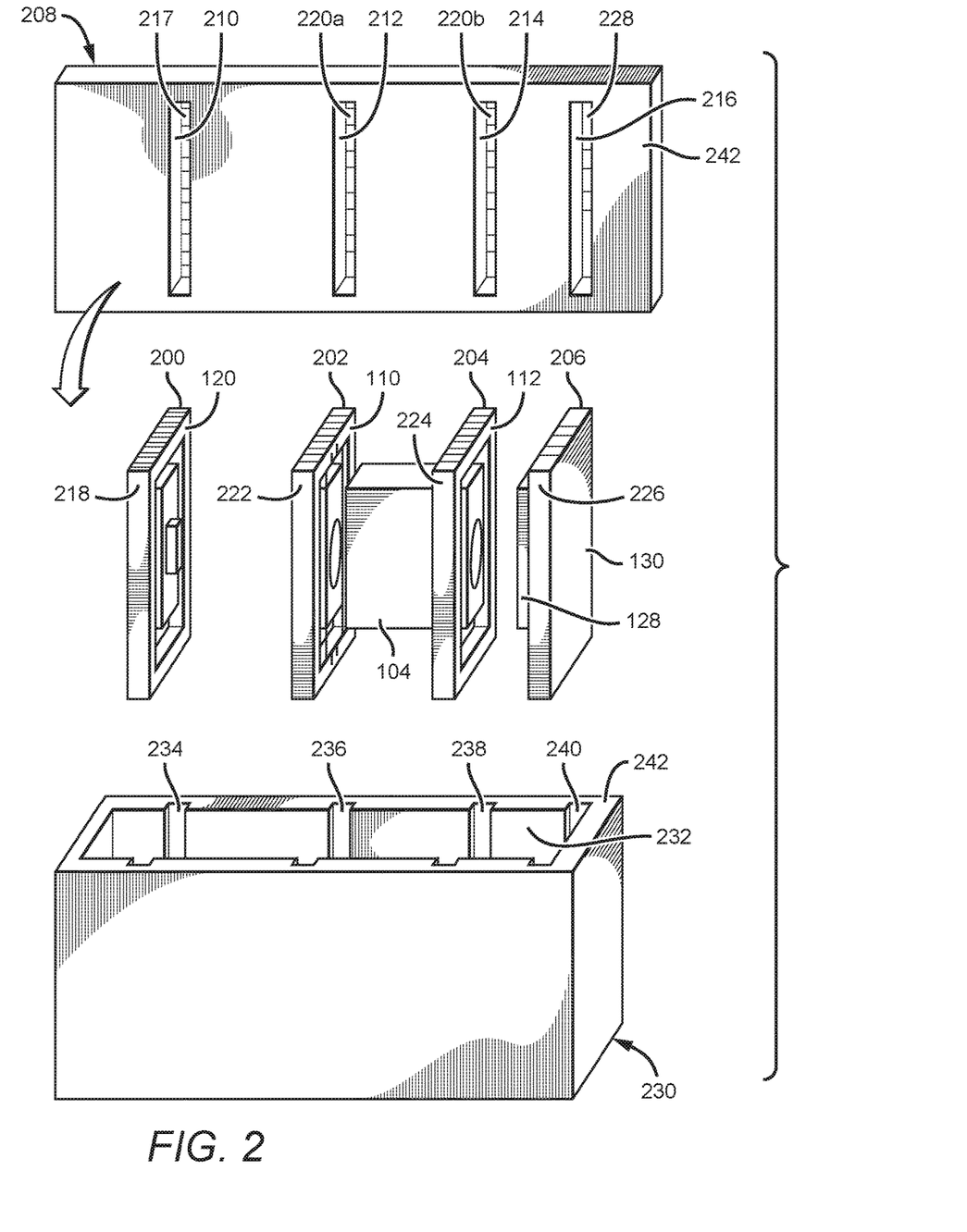
FIGS. 2 and 3 are exploded perspective views of the atomic clock physics package assembly of FIG. 1, with the assembly aligned for slidable coupling within a slotted container and slotted lid having interior electrical contacts.
Figure 3:
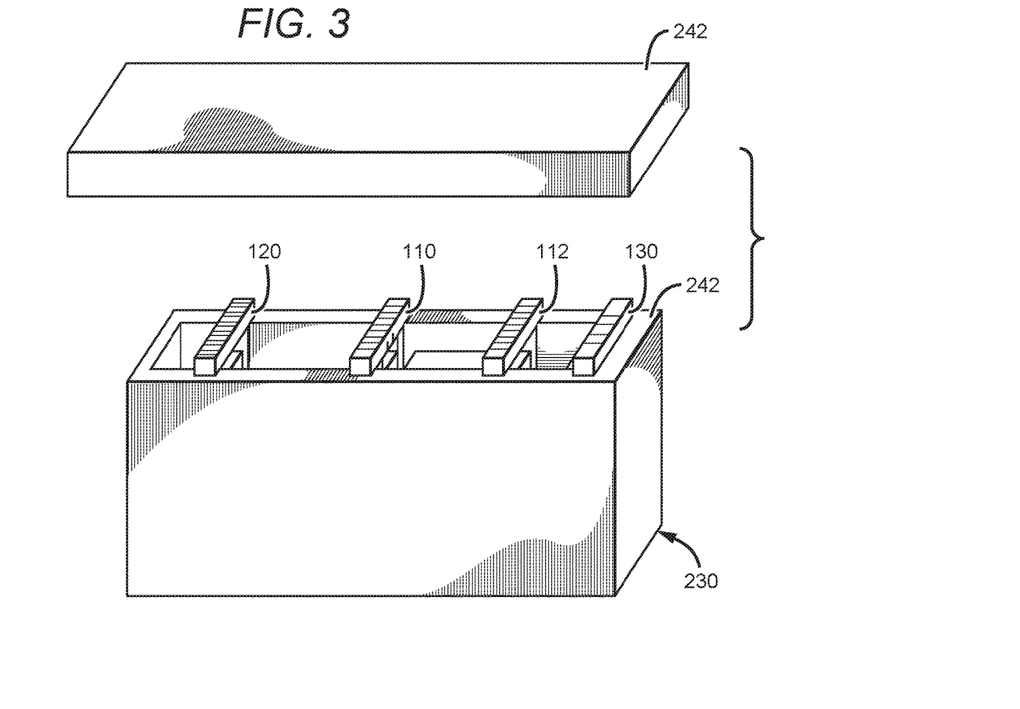

FIGS. 2 and 3 are exploded perspective views of the atomic clock physics package assembly of FIG. 1, with the assembly aligned for slidable coupling within a slotted container and slotted lid. The VCSEL carrier 120, vapor cell carriers (110, 112), and photodetector carrier 130 may have respective electrical carrier contacts (200, 202, 204, 206) for communication of signals and power to their respective coupled components (118 (see FIG. 1), 104, 128). Turning first to the carrier lid 208, the carrier lid 208 may have a VCSEL carrier lid slot 210, first and second vapor cell carrier lid slots (212, 214), and a photodetector carrier lid slot 216 for receipt of respective top portions of each of the carriers (110, 112, 120, 130), as described further below. The VCSEL carrier lid slot 210 may be described as a right rectangular prism shaped slot (alternatively referred to as a channel) having a rectangular aperture in the lid 208. A plurality of VCSEL carrier lid contacts 217 may be disposed on an interior bottom floor of the VCSEL carrier lid slot 210 and in electrical communication with exterior atomic clock pads (not shown). The VCSEL carrier lid slot 210 is dimensioned to slidably receive and guide a top rectangular portion 218 of the VCSEL carrier 120. The VCSEL carrier contacts 200 may be in electrical contact with the VCSEL lid slots 212 when the VCSEL carrier 120 is completely and slidably inserted into the VCSEL carrier lid slot 210 to enable communication of VCSEL control signaling and power between the vapor cell and exterior atomic clock physics package pads (not shown).

Similarly, the lid 208 may have first and second vapor cell carrier lid slots (212, 214) formed as right rectangular prism slots in interior dimension, and each having a rectangular aperture in the lid 208 to receive the vapor cell carriers (110, 112). Either one or both first and second vapor cell carrier lid slots (212, 214) may have vapor cell lid contacts (220a, 220b) disposed on interior bottom floors of them and in communication with exterior atomic clock pads (not shown). The first and second vapor cell carrier lid slots (212, 214) are dimensioned to slidably receive and top rectangular portions (222, 224) of the first and second vapor cell carriers (110, 112), respectively, thereby slidably holding the first and second vapor cell carriers (110, 112) laterally and horizontally, limiting vertical translation, and guiding the vapor cell contacts (202, 204) into electrical contact with the vapor cell lid contacts (220a, 220b). The vapor cell contacts may enable thermistor, heater, coil, and other communications between the vapor cell and the remainder of the assembly.

The photodetector carrier lid slot 216 may also be a right rectangular prism shaped slot having a rectangular aperture in the lid 208. Photodetector lid contacts 228 may be disposed on an interior bottom floor of the photodetector carrier lid slot 216 and in electrical communication with exterior atomic clock physics package pads (not shown). The photodetector carrier lid slot 216 may be dimensioned to slidably receive and guide a top rectangular portion 226 of the photodetector carrier 130 to establish electrical contact between the photodetector lid contacts 228 and the photodetector carrier contacts 206 when the photodetector carrier 130 is completely and slidably inserted into the photodetector carrier slot 216.

Although the contacts (200, 202, 204, 206) are illustrated as relatively flat and on respective top ends of the carriers (120, 110, 112, 130) for electrical connection with lid contacts (217, 220a, 220b, 228), in an alternative embodiment, the carriers may have carrier contacts (200, 202, 204, 206) that are configured differently, such as being U-shaped and capping the top ends of the carriers, being spring loaded, or incorporating a plug and socket configuration. In another embodiment, one or more of the carriers (120, 110, 112, 130) may have a top side that is not at a planar right angle to side portions of the carriers, but rather may form contacts that are angular or nonplanar for receipt into the lid contacts, such as may be the case if the carrier contacts are not embedded in or are not relatively flush on top of the carriers, but rather are formed with flexible metal contacts or contacts which are operable to springily engage lid contacts as the carriers and respective carrier contacts are slidably inserted into the lid slots and abut the respective lid contacts.

The container 230 has an open end 232 and has VCSEL, first and second container vapor cell and photodetector container slots (234, 236, 238, 240). The slots may have a rectangular cross section to accept sides of the respective rigid-framed carriers (120, 110, 112, 130) and may extend into side walls of the container to provide proper alignment and fixed spacing for each of the carriers (120, 110, 112, 130). Each slot may extend from the open end 232 down to a bottom floor (not shown) of the container 230 so that when the carriers (120, 110, 112, 130) are inserted into the container slots (234, 236, 238, 240), the top rectangular portions (218, 222, 224, 226) of the carriers continue to extend beyond the open end 232 (see FIG. 3) for slidable seating in the lid slots (210, 212, 214, 216). Because the rectangular portions (218, 222, 224, 226) of the carriers continue to extend beyond the open end 232, electrical communication may be established between the carrier contacts (200, 202, 204, 206) and the respective lid contacts (217, 220a, 220b, 228). A top sealing surface 242 of the container 230 may be configured to sealably couple with a lid sealing surface 242 of the lid 208 using a sealant such as solder so that a vacuum may be maintained within the container after sealing.

Figure 4:
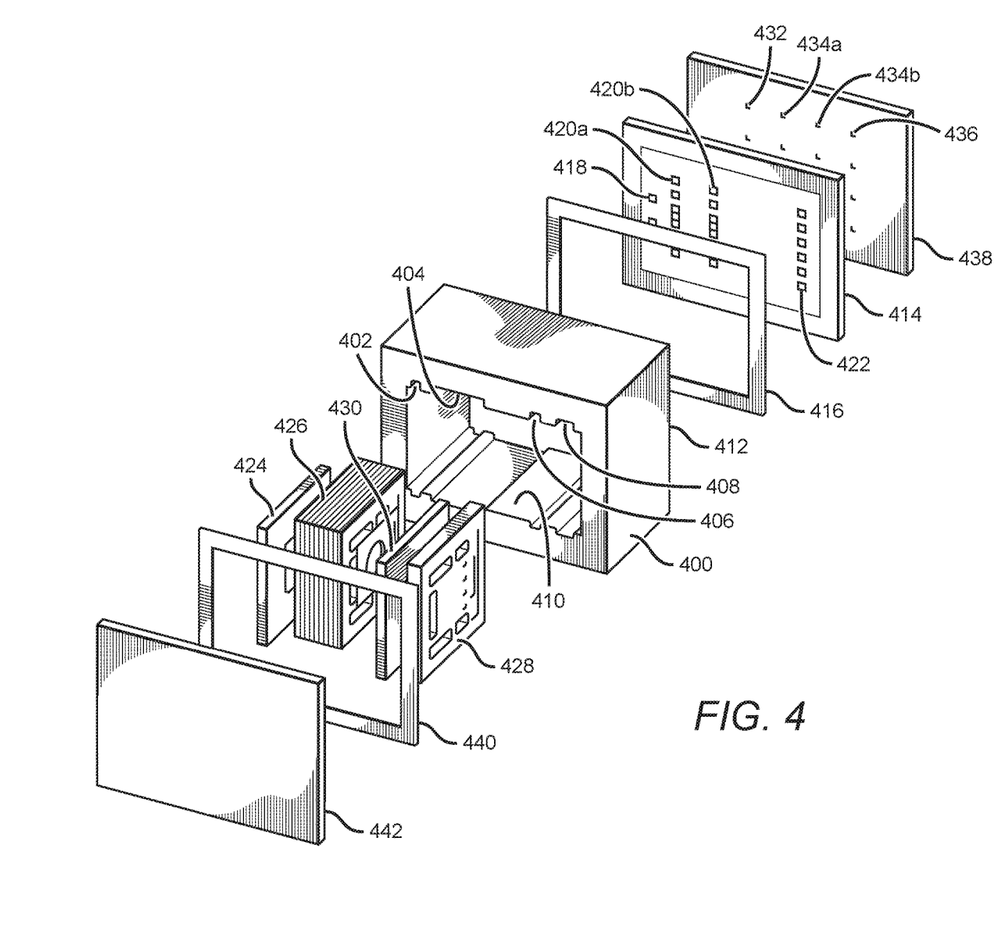
FIGS. 4 and 5 are exploded front perspective views of another embodiment of an atomic clock physics package having a vapor cell, photodetector, and VCSEL laser source that may be removably inserted into a sealable slotted container having interior electrical contacts.
Figure 5:
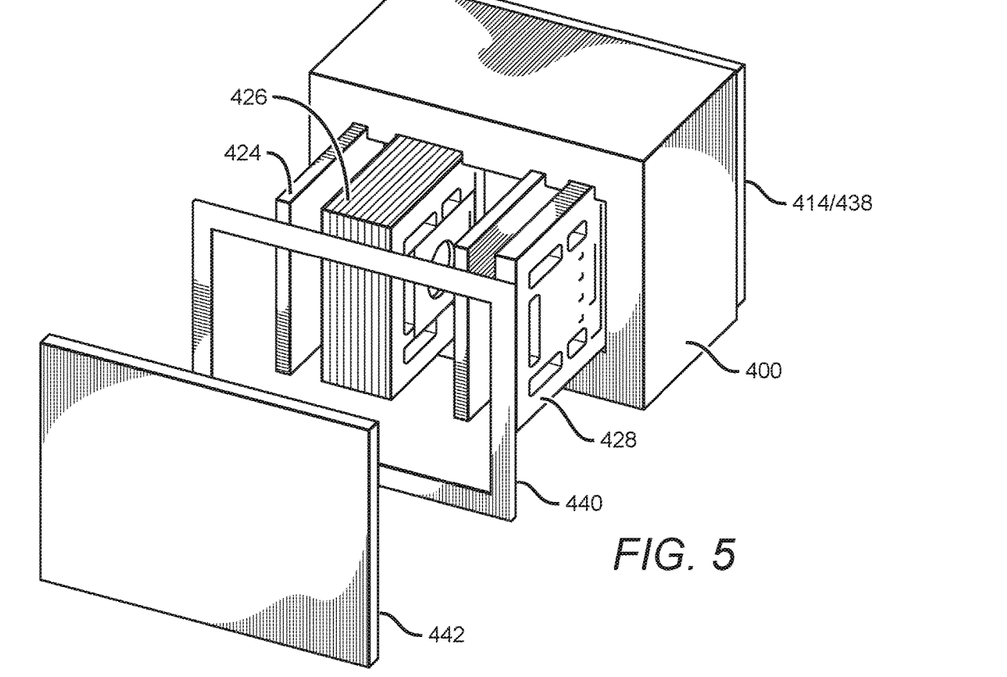

FIGS. 4 and 5 are exploded front perspective views of another embodiment of an atomic clock physics package having a vapor cell, photodetector, and VCSEL laser source that may be removably inserted into a sealable slotted container, subsequent to individual assembly and independent testing, with the slottable container assembly having interior electrical contacts (rather than electrical contacts on the lid) to exchange signals with the vapor cell, photodetector, and VCSEL laser source. The slotted container 400 may have VCSEL, vapor cell, filter and photodetector carrier container slots (402, 404, 406, 408) extending from an open side 410 to a back side 412 of the slotted container 400. A base wall 414 may be sealably coupled to the slotted container 400 at the container's back side 412, such as by using a solder preform 416 during assembly. The base wall 414 may have a plurality of VCSEL, vapor cell, and photodetector electrical container contacts (418, 420a/420b, 422) on or otherwise embedded in the base wall 414. The container contacts (418, 420a/420b, 422) are aligned with a respective plurality of carrier contacts (not shown) when the photodetector, vapor cell and VCSEL carriers (424, 426 428) are inserted into their respective carrier slots (402, 404, 408). An optic such as a wave plate polarizer (not shown) may be coupled to a filter carrier 430 to be slidably received by the filter carrier slot 406. The optic element may be passive (non-electrically addressable), or may be electrically addressable (such as including electro-optic elements), in which for the latter case the carrier and container would include electrical contacts for electrical interconnection to this module. Each of the plurality of slotted container contacts is in electrical communication with a respective plurality of pad substrate vias (432, 434a, 434b, 436) on a pad substrate 438 that are in electrical communication with atomic clock physics package pads (see FIGS. 7, 8, and 9) on an exterior side of the pad substrate 438. A lid solder preform 440 may be used to create a hermetic seal as between the slotted container 400 and the lid 442. In one embodiment, the pad substrate 438 and base wall 414 are two-layer co-fired ceramics.

Figure 6:
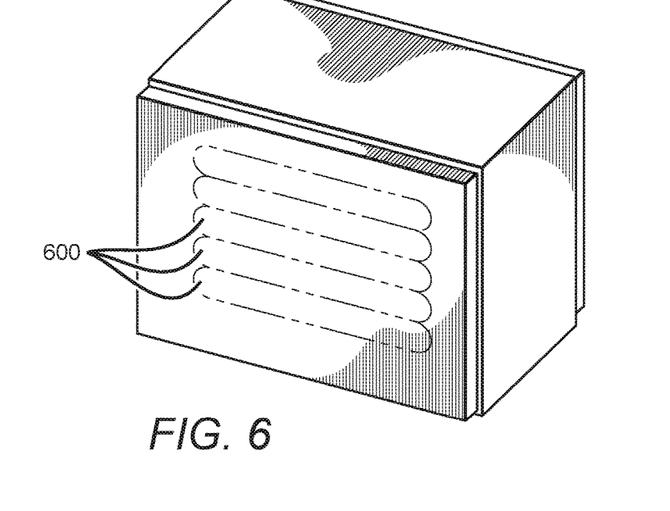
FIG. 6 is a perspective view of the fully assembled slotted container assembly.

FIG. 6 is a perspective view of the fully assembled slotted container assembly. Dashed lines are illustrated on the lid to indicate the locations of interior channels 600 that may be provided for application of getter.

Figures 7, 9:
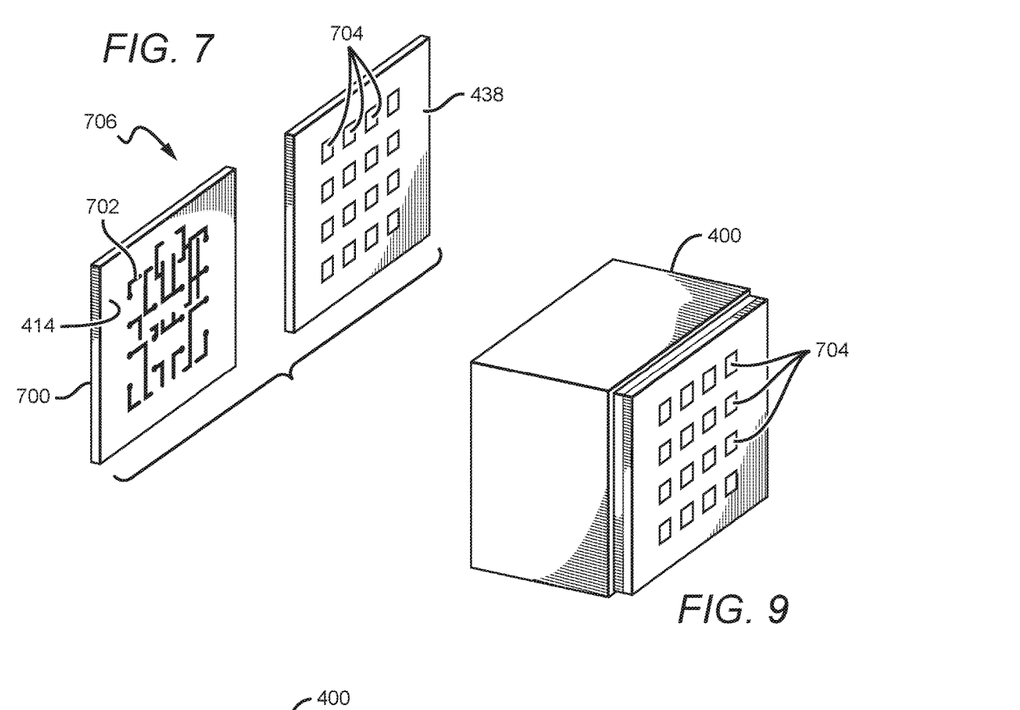
FIGS. 7 and 8 are exploded rear perspective views of the slotted container, base wall and pad substrate first illustrated in the front perspective views of FIGS. 4 and 5.
FIG. 9 is a perspective view of the assembled components illustrated in FIGS. 7 and 8.
Figure 8:
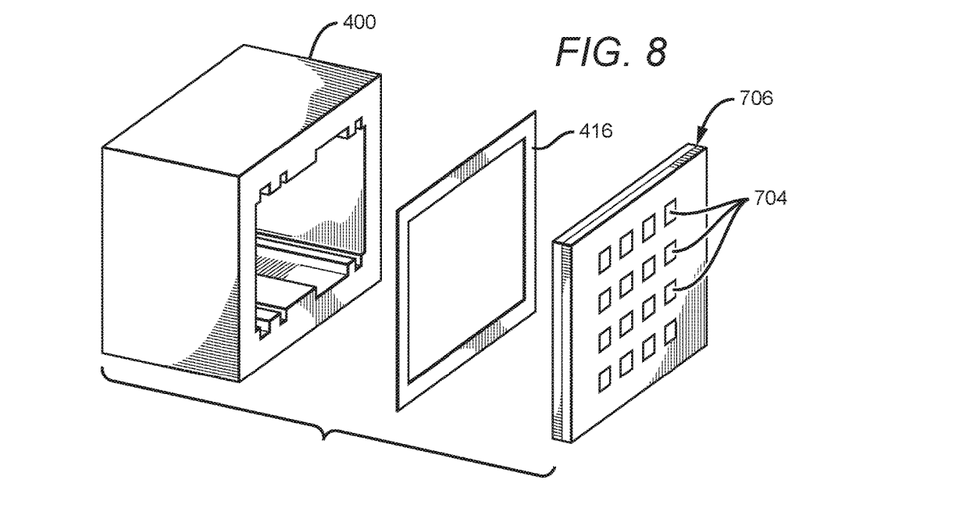

FIGS. 7 and 8 are exploded rear perspective views of the slotted container, base wall and pad substrate first illustrated in the front perspective views of FIGS. 4 and 5. Photodetector electrical container contacts (418, 420a/420b, 422) (see FIG. 4) of the base wall 414 are in electrical communication with rear electrical traces 702 through internal vias (not shown). The pad substrate 438 may have internal conductive vias (not shown) to provide electrical communication between the rear electrical traces 702 and atomic clock physics package pads 704. The base wall 414 may be coupled to the pad substrate 438 to establish a base wall assembly 706. The base wall assembly 706 may be coupled to the slotted container 400 using the solder preform 416. In FIG. 9, the assembly is illustrated fully assembled.

Figure 10:
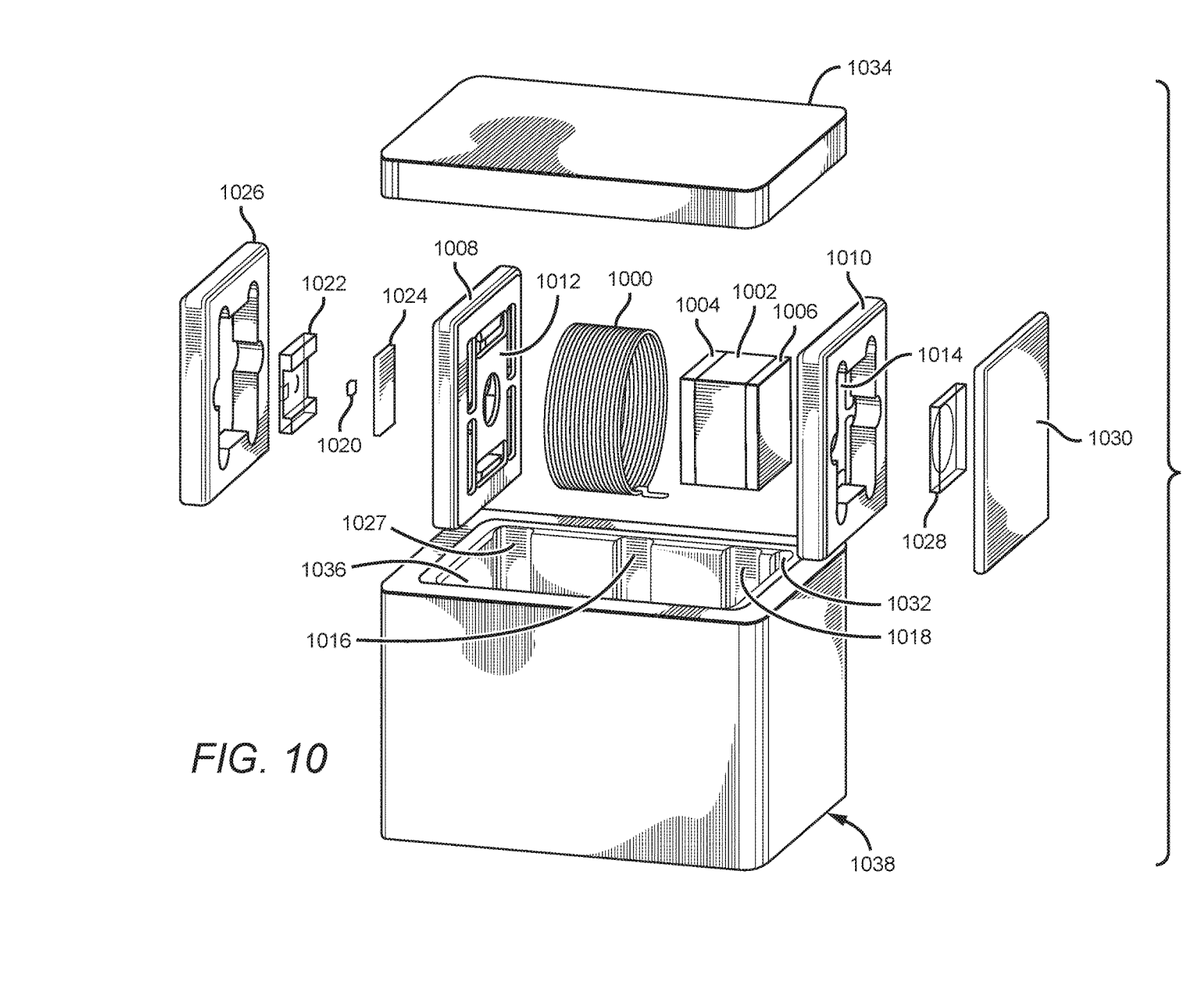
FIGS. 10 and 11 are exploded side perspective views of an atomic clock physics package having a magnetic field coil extending around a vapor cell coupled between first and second vapor cell carriers, with the first and second vapor cell carriers slidably seated into a sealable slotted container.
Figure 11:
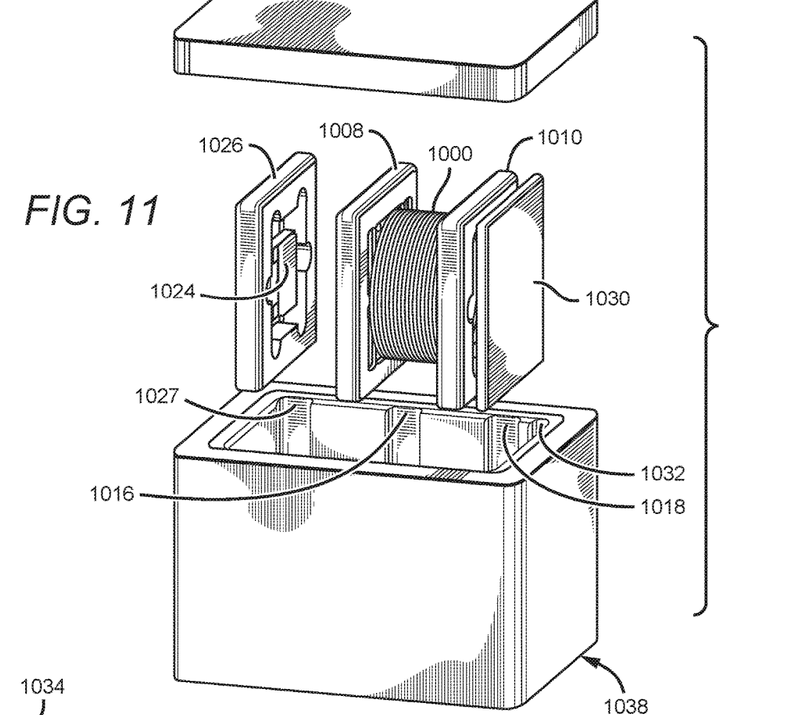
Figure 12:
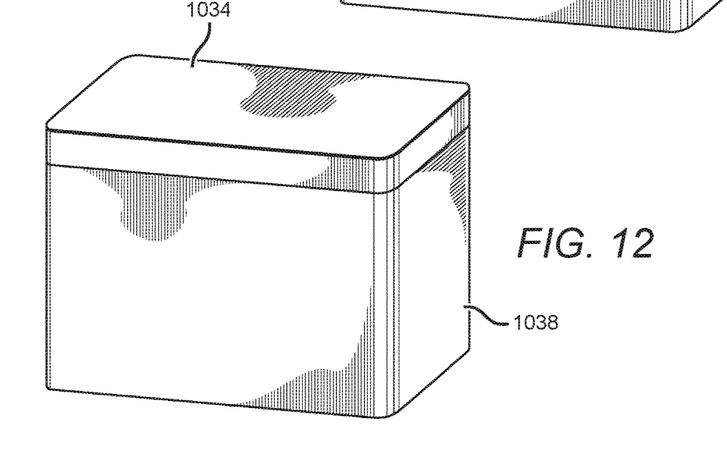
FIG. 12 is a perspective view of the assembled components illustrated in FIGS. 10 and 11.

FIGS. 10 and 11 are exploded side perspective views and FIG. 12 an assembled view of an atomic clock physics package having a magnetic field coil extending around a vapor cell coupled between first and second vapor cell carriers, with the first and second vapor cell carriers slidably seated into a sealable slotted container subsequent to individual assembly and independent testing. The magnetic field coil 1000 may be disposed circumferentially about a vapor cell 1002 to provide a known magnetic field for generating appropriate atomic states in alkali vapor of the vapor cell 1002. The vapor cell 1002 and glass windows (1004, 1006) may be suspended between first and second vapor cell carriers (1008, 1010). Each vapor cell carrier (1008, 1010) may have a respective low thermal dissipation suspension structure (1012, 1014) attached to the frame and extending into a center region of the frame for suspending and thermally isolating the vapor cell from the remainder of the two vapor cell carriers (1008, 1010). The first and second vapor cell carriers (1008, 1010) may be slidably seated into first and second vapor cell carrier slots (1016, 1018).

A VCSEL 1020 may be coupled to a substrate spacer 1022, with a filter package 1024, preferably a wave plate polarizer and ND filter, also coupled to the substrate spacer 1022 and disposed in front of the VCSEL 1020. The substrate spacer 1022 is coupled to the VCSEL substrate carrier 1026 and the VCSEL substrate carrier 1026 slidably seated into a VCSEL substrate carrier slot 1027.

A photodetector 1028 may be seated on a photodetector carrier 1030 that is slidably seated in a photodetector carrier slot 1032. The VCSEL 1020, vapor cell 1002 and photodetector 1020 are positioned so that light emitted from the VCSEL 1020 is directed through the vapor cell 1002 to impinge on the photodetector 1020. A container lid 1034 may have a container facing VCSEL carrier lid slot, first and second vapor cell carrier lid slot, and photodetector carrier lid slot (each not shown) for slideably receiving the respective VCSEL substrate carrier 1026, first and second vapor cell carriers (1008, 1010) and photodetector carrier 1030. The container lid 1034 may also sealably couple to an open end 1036 of the container 1038.

Figures 13, 14:
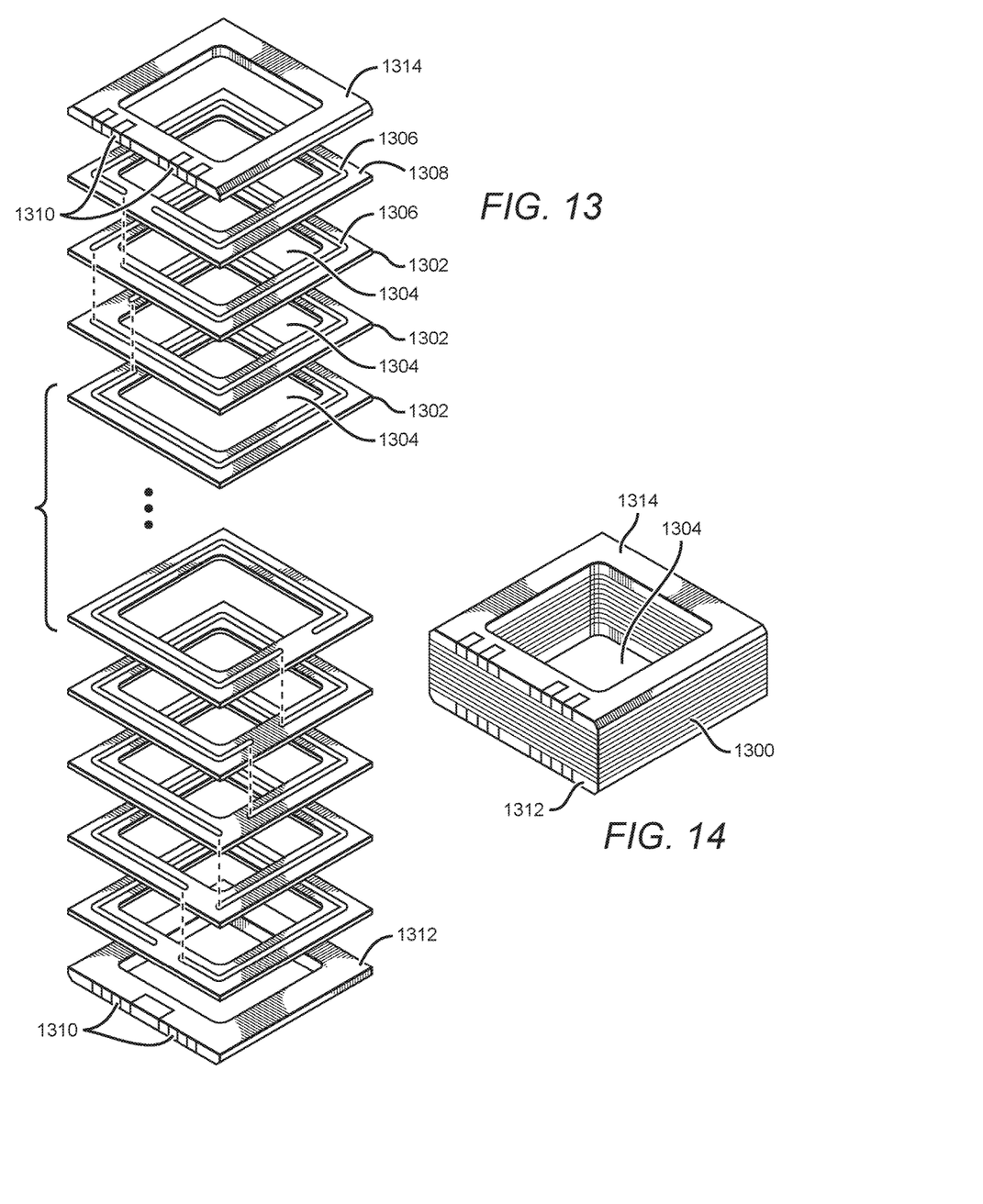
FIGS. 13 and 14 are exploded perspective and assembled perspective views, respectively, of one embodiment of a plurality of partial-loop conductive traces embedded in a multilayered dielectric that collectively form a monolithic coil structure.

FIGS. 13 and 14 are exploded perspective and assembled perspective views, respectively, of one embodiment of a plurality of partial-loop conductive traces embedded in a multilayered dielectric that collectively form a monolithic coil structure. The coil structure may be used to both suspend a vapor cell through low thermal dissipation suspensions while enabling a magnetic field to be applied to the vapor cell. The plurality of dielectric layers 1300, such as layers of ceramic 1302, are positioned in a stacked arrangement, with each ceramic layer 1302 in the shape of a square or rectangular toroid that establishes a center aperture 1304. Each ceramic layer 1302 may have a partial loop conductive trace 1306 extending about its top face 1308, with one end of the conductive trace connected to a via interconnect (not shown) for electrical connection to a pad or other terminal on a bottom face of the ceramic layer for electrical connection to a bottom facing adjacent ceramic layer (electrical connections indicated by dashed lines). The other end of the metal trace on the top face may be connected to a top facing ceramic layer. At either end of the stacked layers of ceramic are vapor cell electrical pads 1310.

In such a manner, the partial-loop conductive traces 1306 are connected serially to create an electrically continuous coil disposed about the center apertures 1304 of the multilayered dielectric to enable a magnetic field to be generated about the aperture 1304 upon application of an electrical signal to the coil. The plurality of via interconnects in the individual layers 1302 may be distributed substantially equally angularly about a perimeter of the plurality of stacked dielectric layers 1302. The assembly may also include a rigid bottom support layer 1312 disposed on a side of the plurality stacked dielectric layers opposite from the rigid top support layer 1314.

Although the illustrated embodiment has a single loop trace on each ceramic layer, in other embodiments each ceramic layer may have two or more loops, depending on size constraints. In such an embodiment, there may be two turns per layer and a total of 16 layers. Each of the partial-loop conductive traces 1306 may have a trace width of 250 microns, a trace thickness of 5 microns, and the two loops be spaced 250 microns apart from one another.

Figures 15, 16:
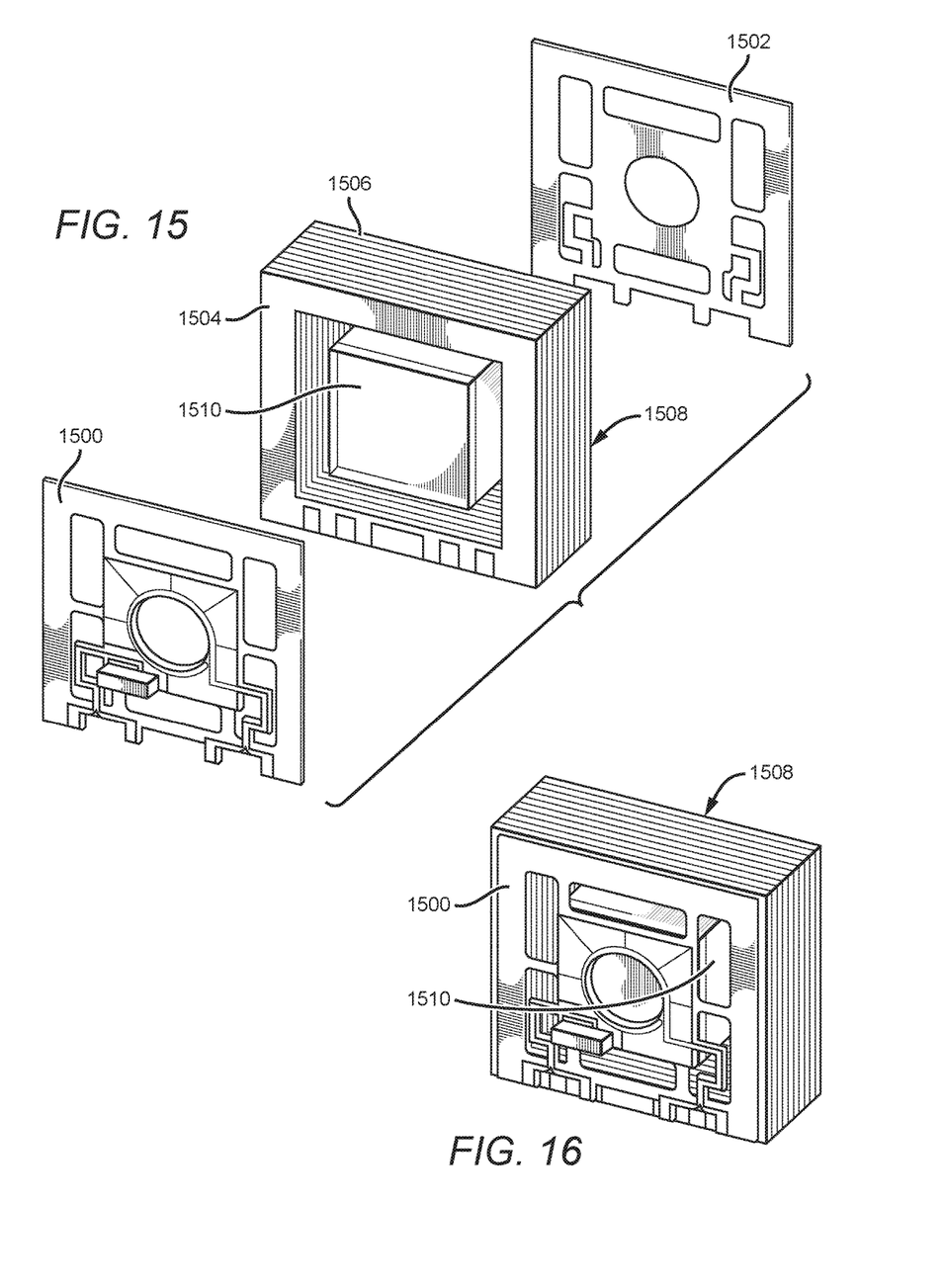
FIGS. 15 and 16 illustrate front and back suspension structures that may be used to support and thermally isolate the vapor cell from the remainder of the atomic clock physics package structure.

FIGS. 15 and 16 illustrate front and back suspension structures that may be used to support and thermally isolate the vapor cell from the remainder of the atomic clock structure. The front and back suspension structures may be front and back low dissipation suspension structures (1500, 1502) made of low thermal conductivity materials, such as Kapton or Cirlex, coupled to first and second sides (1504, 1506) of the plurality of stacked dielectric layers 1508. A vapor cell 1510 may be coupled to the front and back suspension structures (1500, 1502).

Figure 17:
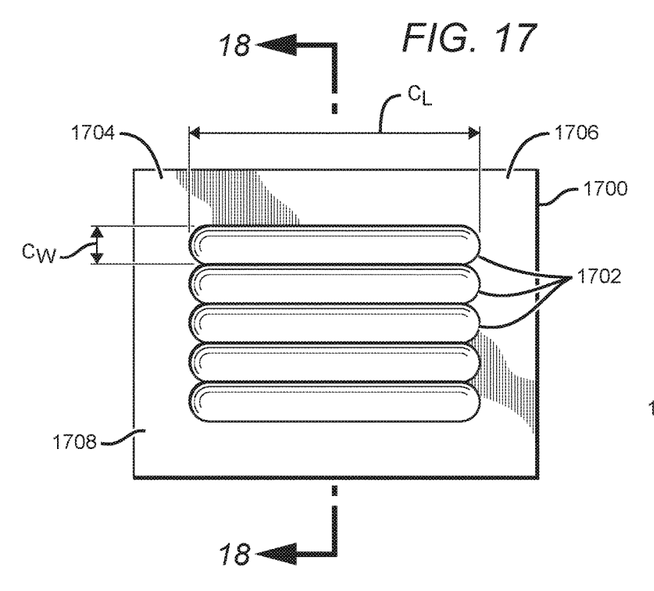
FIGS. 17, 18 and 19 are top plan, side cross-section and perspective views, respectively, of a container lid having surface topology in the form of linear channels for application of a getter coating.
Figure 18:
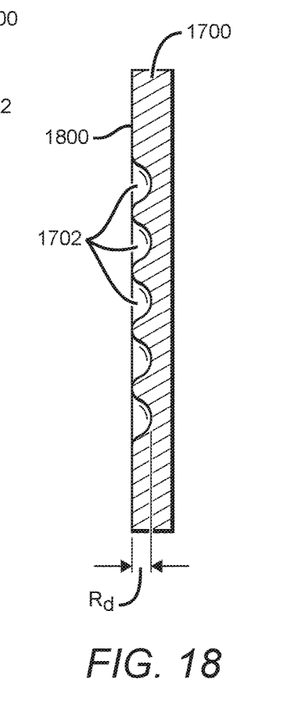
Figure 19:
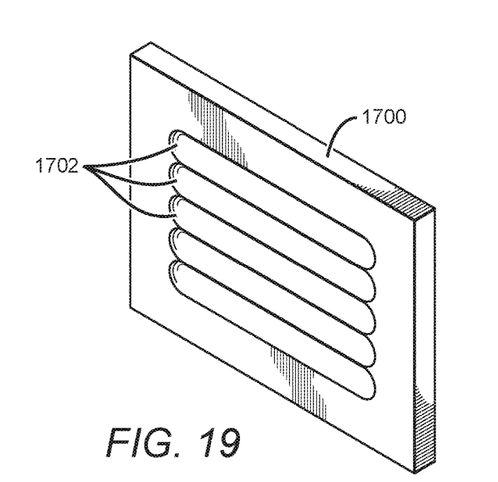

FIGS. 17, 18 and 19 are top plan, side cross-section and perspective views, respectively, of a container lid having getter channels for application of a getter coating to absorb undesirable vacuum gases, such as $O_2$, $H_2O$, $CO$, $CO_2$ and $N_2$, to better maintain the vacuum environment within the hermetically sealed container during use. The lid 1700 may have a metal or ceramic undulating inner surface consisting of a plurality of channels, grooves or troughs ("channels 1702") extending from a first end 1704 to a second end 1706 and extending from an inner surface 1800 of the lid down and into the lid's material. The channels 1702 may extend longitudinally and be spaced apart in a parallel arrangement. In alternative embodiments, the channels extend laterally (i.e., extending between the longer sides of the rectangular lid) or may form a pattern of relatively smooth dimples, rather than channels, that collectively increase the surface area of the inner surface from what would otherwise exist without such dimpling. The channels or dimples, otherwise referred to as an "undulating surface," may be formed by machining, embossing, etching, direct casting, by additive manufacturing or by other methods. By way of example, and not limitation, the getter applied to the channels may be any one of the thin film getters, hydrogen getters, evaporable getters or non-evaporable getters (NEG) offered by SAES Getters S.p.A of Italy.

The channels may have a generally circular or oval cross-section along their length. In one implementation of a container lid having a length of 14.5 mm, a width of 11.0 mm, five channels may be provided having a channel length ($C_L$) of 10 mm, a width ($C_W$) of 1.4 mm and a radial depth (Rd) of approximately 0.5 mm. In such a case, the surface area presented by the undulating surface may have 30% greater surface area than what would otherwise exist without such channels. In other embodiments, the undulating surface may extend up and away from the inner surface 1800 to form longitudinal crowns (now shown), rather than channels extending down into the surface material. Similarly, a dimpled undulating surface may be replaced with a surface having mounds, bumps or other additive material that collectively increase the surface area presented on the inner surface 1800 from what would otherwise exist with a planar surface.

The channels may not extend to the outer perimeter of the container lid, but rather the lid may have a flat and metalized bonding surface 1708 extending about the perimeter to enable coupling and vapor sealing of the lid with a container 1038 (see FIGS. 10-12).

While various implementations of the embodiments have been described, it will be apparent to those of ordinary skill in the art that many more embodiments and implementations are possible that are within the scope of this invention. While reference is made to an atomic clock physics package, this can equally apply to other compact atomic devices, such as magnetometers or gyroscopes.

We claim:

1. A physics package apparatus for a compact atomic device, comprising:
    a container having an interior wall, a first end that is open, a second end oppositely disposed from the first end, and a plurality of slots recessed in the interior wall extending from the first end towards the second end;
    a first vapor cell carrier slidably seated in one of the plurality of slots;
    a vapor cell coupled to the first vapor cell carrier; and
    a lid sealably enclosing the first end;
    wherein the vapor cell is sealably enclosed in the container.

2. The apparatus of claim 1, further comprising:
    a first slot contact disposed in the first one of the plurality of slots; and
    a first vapor cell carrier contact disposed on the first vapor cell carrier, the first vapor cell carrier contact in electrical contact with the first slot contact.

3. The apparatus of claim 2, further comprising:
    a container electrical pad on an exterior surface of the container, the container electrical pad in electrical communication with the first vapor cell carrier contact through the first slot contact.

4. The apparatus of claim 1, further comprising:
    a lid contact disposed on an interior side of the lid; and
    a first vapor cell carrier contact disposed on the first vapor cell carrier, the first vapor cell carrier contact in electrical contact with the lid contact.

5. The apparatus of claim 1, further comprising:
    a photodetector carrier slidably seated in a second one of the plurality of slots.

6. The apparatus of claim 5, wherein the photodetector carrier has a photodetector carrier contact in electrical communication with a lid contact.

7. The apparatus of claim 5, wherein the photodetector carrier has a photodetector carrier contact in electrical communication with a slot contact.

8. The apparatus of claim 1, further comprising a vertical-cavity surface-emitting laser (VCSEL) disposed in a VCSEL carrier, the VCSEL carrier slideably seated in a second of the plurality of slots.

9. The apparatus of claim 8, wherein the VCSEL carrier has a VCSEL carrier contact in electrical communication with a lid contact.

10. The apparatus of claim 8, wherein the VCSEL carrier has a VCSEL carrier contact in electrical communication with a slot contact.

11. The apparatus of claim 8, further comprising:
    a photodetector coupled to a photodetector carrier, the photodetector carrier slidably seated in a third one of the plurality of slots;
    wherein the VCSEL is disposed in complementary opposition to the photodetector through the vapor chamber.

12. The apparatus of claim 1, further comprising:
    an optic coupled to a filter carrier, the filter carrier slidably seated in a second one of the plurality of slots.

13. The apparatus of claim 12, wherein the filter carrier has a filter carrier contact in electrical communication with either a lid contact or a slot contact.

14. The apparatus of claim 1, further comprising solder disposed between the lid and the container to establish a hermetical seal.

15. The apparatus of claim 14, further comprising a vacuum in the container.

16. An apparatus, comprising:
    a container having an interior wall, a first end that is open, a second end oppositely disposed from the first end, and a plurality of carrier slots recessed in the interior wall extending from the first end towards the second end;

a photodetector coupled to a photodetector carrier, the photodetector carrier removably seated in a first carrier slot of the plurality of carrier slots;
a vertical-cavity surface-emitting laser (VCSEL) coupled to a VCSEL carrier, the VCSEL carrier removably seated in a second one of the plurality of carrier slots;
a vapor cell slidably seated in the container; and
a lid sealably enclosing a top side of the container;
wherein the vapor cell, photodetector, and VCSEL are sealably enclosed in the container.

17. The apparatus of claim 16, further comprising:
a first slot electrical contact disposed in the first carrier slot.

18. The apparatus of claim 16, further comprising:
a lid electrical contact disposed on an interior side of the lid.

19. The apparatus of claim 16, further comprising:
an optic coupled to a filter carrier, the filter carrier slidably seated in a third one of the plurality of slots.

20. An apparatus for a compact atomic device, comprising:
a container having a plurality of slots and an open end;
a first vapor cell carrier slidably seated in one of the plurality of slots;
a vapor cell coupled to the first vapor cell carrier;
a lid sealably enclosing the open end, wherein the vapor cell is sealably enclosed in the container;
a lid contact disposed on an interior side of the lid; and
a first vapor cell carrier contact disposed on the first vapor cell carrier, the first vapor cell carrier contact in electrical contact with the lid contact.

21. An apparatus for a compact atomic device, comprising:
a container having a plurality of slots and an open end;
a first vapor cell carrier slidably seated in one of the plurality of slots;
a vapor cell coupled to the first vapor cell carrier;
a lid sealably enclosing the open end, wherein the vapor cell is sealably enclosed in the container; and
at least one carrier selected from the group consisting of:
a photodetector carrier;
a vertical-cavity surface-emitting laser (VCSEL) carrier comprising a VCSEL having a VCSEL carrier contact in electrical communication with a lid contact; and
a filter carrier coupled to an optic,
wherein the at least one carrier is slidably seated in a second one of the plurality of slots.

* * * * *